United States Patent
van Helden et al.

[11] Patent Number: 4,533,379
[45] Date of Patent: Aug. 6, 1985

[54] HERBICIDAL UREA COMPOUNDS

[75] Inventors: Robert van Helden; Frank Baardman; Johannes L. M. Syrier, all of Amsterdam, Netherlands

[73] Assignee: Shell Oil Company, Houston, Tex.

[21] Appl. No.: 504,349

[22] Filed: Jun. 14, 1983

[30] Foreign Application Priority Data

Jun. 25, 1982 [GB] United Kingdom ............... 8218455
Jul. 12, 1982 [GB] United Kingdom ............... 8220141

[51] Int. Cl.³ .................. A01N 43/00; C07D 319/00
[52] U.S. Cl. ........................... 71/88; 549/333; 549/347; 549/373; 564/52
[58] Field of Search ............ 564/52; 549/373, 333; 71/88

[56] References Cited

U.S. PATENT DOCUMENTS

| | | | |
|---|---|---|---|
| 2,655,444 | 10/1953 | Todd | 71/120 |
| 2,655,447 | 10/1953 | Todd | 71/120 |
| 3,342,839 | 9/1967 | Steinbrunn et al. | 564/52 |
| 3,417,085 | 12/1968 | Kuch et al. | 564/52 |
| 3,781,305 | 12/1973 | Teach | 549/373 |
| 4,063,025 | 12/1977 | Murakami et al. | 564/52 |
| 4,260,411 | 4/1981 | Yoshida et al. | 564/52 |

Primary Examiner—Ethel G. Love

[57] ABSTRACT

Novel compounds of the general formula

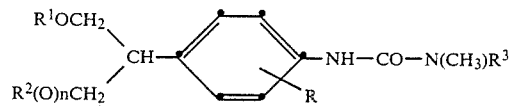

wherein R represents a hydrogen or halogen atom or a (cyclo) alkyl group, $R^3$ represents H, $CH_3$, or $OCH_3$, n=0 or 1, and when n=0, $R^2$ represents a hydrogen atom and $R^1$ a hydrogen atom or a monovalent substituent thereby forming an alkoxide, ether, ester, or other alcohol derivative, and when n=1, each $R^1$ and $R^2$ independently represents one of the atoms specified for $R^1$ when n=0, or $R^1$ and $R^2$ together represent a bivalent group thereby forming a cyclic ether, ester, or other diol derivative, have useful herbicidal properties.

9 Claims, No Drawings

HERBICIDAL UREA COMPOUNDS

BACKGROUND OF THE INVENTION

1. Field of the Invention

This application relates to certain urea compounds, herbicidal compositions containing them and a method of combating undesired plant growth using them.

2. Description of the Prior Art

Certain substituted phenylurea compounds or derivatives are known to be active herbicides, for example, see U.S. Pat. Nos. 2,655,444 to 2,655,447. It has now been found that certain novel substituted phenylurea compounds also have useful herbicidal properties.

SUMMARY OF THE INVENTION

The present invention provides a urea compound of the general formula I

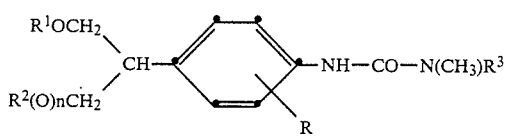

wherein R represents a hydrogen or halogen atom or a (cyclo)alkyl group, $R^3$ represents H, $CH_3$ or $OCH_3$, $n=0$ or 1, and when $n=0$, $R^2$ represents a hydrogen atom and $R^1$ a hydrogen atom, or a monovalent substituent thereby forming an alkoxide, ether, ester, or other alcohol derivative, and when $n=1$, each of $R^1$ and $R^2$ independently represents one of the atoms or groups specified for $R^1$ when $n=0$, or $R^1$ and $R^2$ together represent a bivalent group thereby forming a cyclic ether, ester, or other diol derivative.

The present novel compounds can be viewed as derivatives from 2-(4-(3-methylureido)-phenyl)-1(,3)-propan(edi)ol, i.e. the compound according to formula I wherein $R=R^1=R^2=R^3=H$. It has been found that the present compounds are useful for combating undesirable plant growth and exhibit herbicidal activity, in particular when the substituent groups are not too large. Preferably each of the groups contains up to 13 carbon atoms.

The ring substituent represented by R may be a halogen atom, suitably fluorine, chlorine or bromine. Preferably R represents a chlorine atom. In a second, suitable embodiment R represents an alkyl or a cycloalkyl group, e.g. methyl, ethyl, propyl, isopropyl, cyclopropyl, butyl, pentyl, hexyl and the like. Alkyl groups having up to four carbon atoms are preferred, and in particular R represents a methyl group. Whatever the nature of the ring substituents is, it is of advantage if R represents an atom or a group positioned meta to the methylureido group, i.e. meta to the —NH—CO—N($CH_3$)$R^3$ substituent. Finally R may very suitably represent a hydrogen atom, in other words, the aromatic ring may very well be unsubstituted, except for the two groups already drawn in formula I.

$R^1$, or each of $R^1$ and $R^2$ independently, may represent a hydrogen atom or a monovalent substituent (atom or group) thereby forming an alkoxide, ether, ester or other alcohol derivative. When $n=1$, each of $R^1$ and $R^2$ preferably represents the same. If $R^1$ or $R^2$ represents a hydrogen atom, an alcohol group is formed; otherwise a derivative of the said alcohol group is formed. Suitably $R^1$, or each of $R^1$ and $R^2$ independently, represents a hydrogen atom, a metal (Na, K, Cs for example), an optionally substituted hydrocarbyl group, or a group X derived from an acid XOH. Thus the following alcohol derivatives are formed, respectively: alkoxides, ethers and esters.

The hydrocarbyl group forming an ether may be aliphatic or aromatic and unsaturated bonds may be present therein. The group X is defined in general as the group formed by removing a hydroxy group from any acid, organic or inorganic. It may be viewed as to have been derived from an organic acid, such as a carboxylic acid, a carbamic acid, or a sulphonic acid, or from an inorganic acid such as sulphuric, carbonic or (per)-chloric acid, the only proviso being that the acid (theoretically at least) contains a hydroxy group. The acid itself does not have to be a stable compound, for instead of the acid e.g. a (stable) acid chloride or anhydride can be used to prepare the ester. Preferably $R^1$, or each of $R^1$ and $R^2$ independently, represents a hydrogen atom or an alkyl, aryl, aralkyl, alkanoyl, aroyl, or aralkanoyl group, in particular containing up to four aliphatic carbon atoms. This includes for example for $R^1$ and $R^2$: methyl, ethyl, benzyl, acetyl, and benzoyl groups.

On the other hand, when $n=1$, $R^1$ and $R^2$ very advantageously together may represent a bivalent group, thereby forming a cyclic ether or ester of general formula Ia:

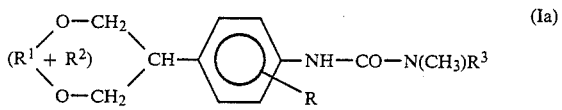

The bivalent group connects the two oxygen atoms, thus forming a ring of at least six members. A six-membered ring is preferred, in other words: preferably a 1,3-dioxane moiety or a derivative or analogue thereof is present in the compound of formula Ia. Suitably $R^1$ and $R^2$ together represent a (cyclo)alkylene or a (cyclo)alkylidene group, or a group Y derived from an acid Y(OH)$_2$. The group Y is defined as the group formed by removing two hydroxy groups from a multibasic acid, organic or inorganic.

When $R^1$ and $R^2$ together represent a (cyclo)alkylene group, the resulting compound of formula Ia contains a cyclic di(ether) unit. For instance, when $R^1$ and $R^2$ represent a trimethylene group, the compound contains an eight-membered dioxocane ring, i.e. a crown ether unit. When $R^1$ and $R^2$ together represent a (cyclo)alkylidene group, the resulting compound of formula Ia again contains a cyclic (di)ether, which might more specifically be named a cyclic formal, acetal or ketal, depending upon the number of hydrogen atoms attached to the carbon atom connecting the two oxygen atoms. By definition the ring is six-membered, if $R^1$ and $R^2$ together represent a (cyclo)alkylidene group. Finally, when $R^1$ and $R^2$ together represent a group Y, the ester of a diol with a multibasic acid is formed. When the group Y is inorganic, the resulting cyclic (di)ester usually has a six-membered ring.

Advantageously $R^1$ and $R^2$ together represent a methylene group, thereby forming a cyclic formal, and (considering the compound from a different viewpoint) a 1,3-dioxane ring:

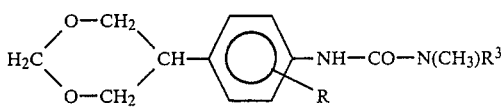

In particular $R^1$ and $R^2$ together represent a 2-butylidene or a 3-pentylidene group.

Alternatively $R^1$ and $R^2$ very suitably together represent a cyclopentylidene group, thereby forming a cyclic ketal. The resulting 1,3-dioxane ring is connected via a spiro-carbon atom to a cyclopentane ring:

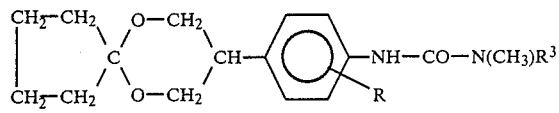

Suitable groups Y include the inorganic CO (carbonyl), SO (sulfinyl), $SO_2$ (sulfonyl), SeO (seleninyl), $SeO_2$ (selenonyl), POH (hydroxyphosphinidene) and P(O)OH (hydroxyphosphinylidene) group, the $PC_6H_5$ (phenylphosphinidene) group, and the organic alkanedioyl group $(CO-(CH_2)_n-CO$, wherein $n=0, 1, 2, 3$ in particular). The hydroxy groups of the phosphorus groups Y may be replaced by any one of the usual halides F, Cl, Br and I of pseudohalides such as CN or NCO. The resulting esters of the inorganic groups Y may also be named as inorganic salts, i.e. as the carbonate, sulphite, sulphate, selenite, selenate, orthophosphite, and orthophosphate, respectively, of the diol compound of formula I, wherein $R^1=R^2=H$.

Good results are obtained when $R^1$ and $R^2$ together represent the sulfinyl group SO, thereby forming a cyclic ester (sulphite):

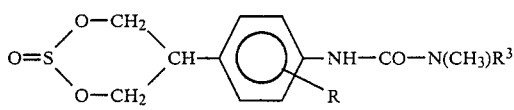

As already stated, the group R in these formulas preferably represents $CH_3$ or Cl, at the position meta to the ureido-group. The best herbicidal results are obtained when $R^3$ represents a methyl group.

The invention also provides a process for the preparation of a compound according to the invention, which comprises preparing the compound in a way which is known per se for analogous compounds, in particular reacting an aniline of the general formula II or a hydrohalide salt thereof:

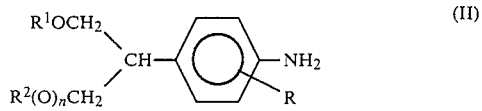

with either (a) a carbamoyl halide $HalCON(CH_3)R^3$, e.g. dimethylcarbamoyl halide, preferably chloride; or (b) phosgene $(COCl_2)$, to produce an isocyanate of formula III, and reacting at least part of the isocyanate with $HN(CH_3)R^3$ e.g. dimethylamine.

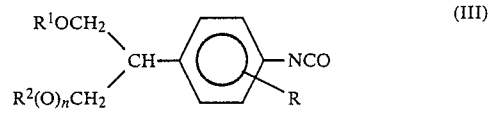

The substituents R, $R^1$ and $R^2$ may have the same meanings as in formula I: however, the conversion of the aniline of formula II (steps (a) or (b)) need not necessarily take place after the introduction of the substituents R, $R^1$ and/or $R^2$. The said conversion may also be carried out in the aniline of formula II wherein some or all of R, $R^1$ and $R^2$ represent H, after which any required substitutions are made in the isocyanate of formula III, or in the urea compound of formula I if desired.

Process (a) may be carried out with or without a solvent. Suitable solvents include hydrocarbons and halogenated hydrocarbons, for example benzene, toluene or carbon tetrachloride. Preferably it is carried out under substantially anhydrous conditions. Since the reaction is a condensation reaction involving the elimination of hydrogen halide it is preferably carried out in the presence of a dehydrohalogenating agent; organic or inorganic bases are suitable; sodium acetate has been found to be especially useful when working without a solvent, and organic bases such as triethylamine or pyridine are suitable when using a solvent. The reaction is preferably carried out at a temperature in the range of from 0° to 80° C., conveniently at room temperature, and the reaction mixture may be worked up by conventional means.

Process (b) is suitably carried out in the presence of a solvent, for example a hydrocarbon, e.g. toluene, at a temperature in the range of from 80° to 120° C.; conveniently, the reaction may be carried out at the reflux temperature of the solvent used. If desired, the resulting isocyanate of formula III may be isolated from the reaction mixture, but preferably it is reacted in situ (di)methylamine. This reaction is suitably carried out at a temperature in the range of from 0° to 30° C., conveniently at room temperature. The desired product may be isolated by any suitable method.

The starting compound of formula II is advantageously prepared form a compound of formula IV, when $n=0$,

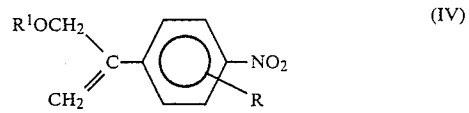

by a hydrogenation of the nitro group and the double bond, and—in so far as necessary—either preceded by or followed by a substitution with the group(s) or atom(s) represented by R.

The starting compound of formula II is advantageously prepared from a compound of formula V, when $n=1$,

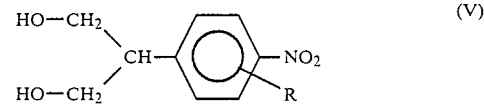

by a hydrogenation of the nitro group and—in so far as necessary—either preceded by or followed by a substitution with the group(s) or atom(s) represented by R, $R^1$ and $R^2$ in formula II.

The hydrogenation may be carried out by catalytic hydrogenation using molecular hydrogen or otherwise, e.g. by a metal and an acid. Conveniently a solution of the nitro compound in an alcohol is agitated with finely divided nickel or platinum under hydrogen gas, at a temperature in the range of 0°–80° C., e.g. room temperature. Alternatively, hydrochloric acid may be added to a mixture of the nitro compound and a metal, e.g. granulate tin, at 50° to 100° C., or ammonium(bi)sulfide may be added to an aqueous/alcoholic solution of the nitro compound. The substitution with the group(s) or atom(s) represented by $R^1$ and $R^2$ may also be carried out in any known manner, e.g. esters may be prepared by reaction with an acid or an acid anhydride or chloride, and alkoxides may be prepared by reaction with metallic Na or K. The compound of formula V is easily prepared from the corresponding (substitute) p-nitrotoluene

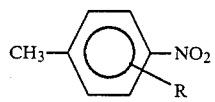

by reaction with formaldehyde in the presence of a base, e.g. potassium alkoxide, at 20°–100° C. in a solvent like dimethylformamide, yielding a 1,3-propanediol compound according to formula V. The compound can be converted into a 1,3-dichloropropane compound, which can be dehydrohalogenated (by the action of a base) to a chloropropylene compound, which may be converted with a suitable agent, e.g. $NaOR^1$, into the desired compound of formula IV.

The compounds of general formula I exhibit herbicidal activity. Therefore the invention further provides a herbicidal composition, which comprises a compound according to formula I, together with a carrier.

The invention also provides a method of combating undesired plant growth at a locus, which comprises applying to the locus a compound or a composition according to the invention. A preferred method of combating undesirable plant growth is to use a compound of the invention in a herbicidally-effective amount. Application may be pre- or post-emergence. Dosages of active ingredient may range e.g. from 0.05 to 5 kg/ha.

A carrier in a composition according to the invention is any material with which the active ingredient is formulated to facilitate application to the locus to be treated, which may for example be a plant, seed or soil, or to facilitate storage, transport or handling. A carrier may be a solid or a liquid, including a material which is normally gaseous but which has been compressed to form a liquid, and any of the carriers normally used in formulating herbicidal compositions may be used. Preferably compositions according to the invention contain 0.5 to 95% by weight of active ingredient.

Suitable solid carriers include natural and synthetic clays and silicates, for example natural silicas such as diatomaceous earths; magnesium silicates, for example talcs; magnesium aluminium silicates, for example attapulgites and vermiculites; aluminium silicates, for example attapulgites and vermiculites; aluminium silicates, for example kaolinites, montmorillonites and micas; calcium carbonate; calcium sulphate; synthetic hydrated silicon oxides and synthetic calcium or aluminium silicates; elements, for example carbon and sulphur; natural and synthetic resins, for example coumarone resins, polyvinyl chloride, and styrene polymers and copolymers; solid polychlorophenols; bitumen; waxes, for example beeswax, paraffin wax, and chlorinate mineral waxes; and solid fertilisers, for example superphosphates.

Suitable liquid carriers include water; alcohols, for example isopropanol and glycols; ketones, for example acetone, methyl ethyl ketone, methyl isobutyl ketone and cyclohexanone; ethers; aromatic or araliphatic hydrocarbons, for example benzene, toluene and xylene; petroleum fractions, for example kerosine and light mineral oils; chlorinated hydrocarbons, for example carbon tetrachloride, perchloroethylene and trichloroethane. Mixtures of different liquids are often suitable.

Agricultural compositions are often formulated and transported in a concentrated form which is subsequently diluted by the user before application. The presence of small amounts of a carrier which is a surface-active agent facilitates this process of dilution. Thus preferably at least one carrier in a composition according to the invention is a surface-active agent. For example the composition may contain at least two carriers, at least one of which is a surface-active agent.

A surface-active agent may be a emulsifying agent, a dispersing agent or a wetting agent; it may be nonionic or ionic. Examples of suitable surface-active agents include the sodium or calcium salts of polyacrylic acids and lignin sulphonic acids; the condensation products of fatty acids or aliphatic amines or amides containing at least 12 carbon atoms in the molecule with ethylene oxide and/or propylene oxide; fatty acid esters of glycerol, sorbitan, sucrose or pentaerythritol; condensates of these with ethylene oxide and/or propylene oxide; condensation products of fatty alcohol or alkyl phenols, for example p-octylphenol or p-octylcresol, with ethylene oxide and/or propylene oxide; sulphates or sulphonates of these condensation products; alkali or alkaline earth metal salts, preferably sodium sats, of sulphuric or sulphonic acid esters containing at least 10 carbon atoms in the molecule, for example sodium lauryl sulphate, sodium secondary alkyl sulphates, sodium salts of sulphonated caster oil, and sodium alkylaryl sulphonates such as sodium dodecylbenzene sulphonate; and polymers of ethylene oxide and copolymers or ethylene oxide and propylene oxide.

The compositions of the invention may for example be formulated as wettable powders, dusts, granules, solutions, emulsifiable concentrates, emulsions, suspension concentrates and aerosols. Wettable powders usually contain 25, 50 or 75% w of active ingredient and usually contain, in addition to solid inert carrier, 3–10% w of a dispersing agent and, where necessary, 0–10% w of stabiliser(s) and/or other additives such as penetrants or stickers. Dusts are usually formulated as a dust concentrate having a composition similar to that of a wettable powder but without a dispersant, and are diluted in the field with further solid carrier to give a composition usually containing 0.5–10% w of active ingredients. Granules are usually prepared to have a size between 10 and 100 BS mesh (1.676–0.152 mm), and may be manufactured by agglomeration or impregnation techniques. Generally, granules will contain 0.5–25% w active ingredient and 0–10% w of additives such as stabilisers, slow release modifiers and binding agents. The so-called "dry-flowable powders" consist of relatively small granules having a relatively high concentration of active ingredient. Emulsifiable concentrates usually contain, in addition to a solvent and, when necessary, cosolvent, 10–50% w/v active ingredient, 2–20% w/v emulsifiers and 0.20% w/v of other additives such as stabilisers, penetrants and corrosion inhibitors. Suspension concentrates are usually compounded so as to obtain a stable, non-sedimenting flowable product and usually contain 10–70% w active ingredient, 0.5–15% w of dispersing agents, 0.1–10% w of suspending agents such as protective colloids and thixotropic agents, 0–10% w of other additives such as defoamers, corrosion inhibitors, stabilisers, penetrants and stickers, and water or an organic liquid in which the active ingredient is substantially insoluble; certain organic solids or inorganic slats may be present dissolved in the formulation to assist in preventing sedimentation or as antifreeze agents for water.

Aqueous dispersions and emulsions, for example compositions obtained by diluting a wettable powder or a concentrate according to the invention with water, also lie within the scope of the present invention. The said emulsions may be of the water-in-oil or of the oil-in-water type, and may have a thick "mayonnaise"-like consistency.

The compositions of the invention may also contain other pesticidal ingredients, for example, other compounds possessing insecticidal, herbicidal or fungicidal properties.

The following Examples illustrate the invention. NMR values are chemical shifts in ppm, relative to tetramethylsilane, in CDCl$_3$.

EXAMPLE 1

3-(4-(3,5-dioxacyclohexyl)-3-methylphenyl)-1,1-dimethylurea (formula Ia, wherein R=R$^3$=CH$_3$, R$^1$+R$^2$=CH$_2$)

(a) A mixture of 4-nitro-o-xylene (52.5 g; 0.35 mol), paraformaldehyde (28.7 g; 0.96 mol) and DMF (175 ml) was stirred at 25° C. in an oil bath. A slurry of potassium tert-butoxide (12.6 g; 0.11 mol) in tert.butanol (40 ml) was added in 5 minutes. After 15 minutes the temperature was slowly raised to 50°–60° C. After 4 hours at 50°–60° C., the mixture was allowed to cool to room temperature, acidified with 10 ml conc.HCl and then poured into a mixture of water (1.2 l) and ethyl acetate (200 ml).

A first batch of solid material was collected by filtration, washed first with water, then with ethyl acetate and pentane, and dried in vacuo at 50° C.

The combined organic layers of the filtrates were washed with aq. NaCl, dried over MgSO$_4$ and evaporated at reduced pressure. The residue was taken up in chloroform, the solids were filtered off and stirred with pentane to remove unconverted starting material. After filtration, this second batch of solid material was dried in vacuo at 50° C.

Both batches consisted of a yellow powder of 2-(2-methyl-4-nitrophenyl)-1,3-propanediol, the first batch comprising 29.3 g (purity 98.7%) and the second batch comprising 12.4 g (purity 94.7%). The total molar yield was 55%.

(b) The compound prepared in (a) (2.6 g; 12.3 mmol) and paraformaldehyde (0.6 g; 20 mmol) were taken up in toluene (30 ml), and a catalytic amount of p-toluene-sulphonic acid was added. The solution was stirred in an oil bath at 110° C. After half an hour all the starting material had been converted. The solution was heated under reflux, with stirring, for another half hour in order to remove water by means of a Dean-Stark trap. The excess paraformaldehyde was removed simultaneously by sublimation to the walls of the reaction vessel and the cooler. The solvent was evaporated and the remaining solid (2.6 g) consisted of 4-(3,5-dioxacyclohexyl)-3-methylnitrobenzene (purity >99%; yield 95%).

(c) The 4-(3,5-dioxacyclohexyl)-3-methylnitrobenzene prepared in (b) (2.6 g; 11.7 mmol) was dissolved in methanol (50 ml) and a catalytic amount of 10% Pt/C was added. The reduction was carried out at room temperature, in a hydrogenation apparatus operating at atmospheric pressure. ~750 ml H$_2$ (~30 mmol) was taken up in 2 hours. After removal of the catalyst by filtration, the reaction mixture was evaporated to dryness.

4-(3,5-Dioxacyclohexyl)-3-methylaniline was isolated in quantitative yield.

(d) The compound prepared in (c) (2.5 g; 13.0 mmol) was taken up in ethyl acetate (15 ml) and added to a saturated solution of phosgene in toluene (35 ml), with stirring at room temperature. The reaction mixture was slowly heated to reflux and a vigorous stream of dry nitrogen was passed through the solution, in order to remove the HCl formed, and the excess COCl$_2$. After about 1 hour the reaction mixture was allowed to cool to room temperature and a saturated solution of dimethylamine in toluene (20 ml) was added. After about 1 hour a precipitate was formed. The white solid was filtered off and recrystallized from toluene/cyclohexane/ethyl acetate to yield the desired urea derivative (purity >95% 1.7 g; 6.44 mmol=50% yield (unoptimized)). The NMR spectrum of the compound is as follows: δ2.35 (3H,s), 3.0 (6H,s), 3.4 (1H,m), 3.65–4.25 (4H,m), 4.73 (1H,d), 5.1 (1H,d), 6.35 (1H,s), 6.93–7.35 (3H;complex).

EXAMPLE 2

3-(4-(1,5-dioxaspiro[5.5]undec-3-yl)-3-methylphenyl)-1,1-dimethylurea (formula Ia, wherein R=R$^3$=CH$_3$, R$^1$+R$^2$=cyclohexylidene)

(a) 2-(2-Methyl-4-nitrophenyl)-1,3-propanediol was prepared as described in Example 1(a).

(b) A quantity of 2.1 g (10 mmol) thereof and a quantity of 1.1 g of cyclohexanone (11 mmol) were taken up in toluene (30 ml), and a catalytic amount of p-toluene-sulphonic acid was added. The solution was heated under reflux with stirring, while water was removed continuously by means of a Dean-Stark trap. When the separation of water ceased (after about one hour), the solvent was evaporated. The remaining solid (2.8 g) consisted of 4-(1,5-dioxaspiro[5.5]undec-3-yl)-3-methyl nitrobenzene (purity 90%; yield 96%).

(c),(d) The compound thus prepared was converted into its urea derivative by the procedure as described in Example 1 (c) and (d). The final product consisted of 2.3 g of the title compound (purity >90%; yield 73% molar).

The NMR spectrum is as follows: δ1.2–2.1 (10H,complex), 2.35 (3H,s), 3.0 (6H,s), 3.3 (1H,m), 3.65–4.2 (4H,m), 6.3 (1H,s), 7.1–7.3 (3H,complex).

In an *alternative preparation*, the order of the hydrogenation and the introduction of the cyclohexylidene group were reversed:

(b') 2-(2-Methyl-4-nitrophenyl)-1,3-propanediol (5.0 g; 23.7 mmol) was dissolved in methanol (50 ml) and a catalytic amount of 10% Pt/C was added. The reduction was carried out at room temperature, in a hydrogenation apparatus operating at atmospheric pressure. ~2 l H$_2$ (~80 mmol) was taken up. After removal of the catalyst by filtration the reaction mixture was evaporated to dryness.

2-(4-Amino-2-methylphenyl)-1,3-propanediol was isolated in quantitative yield.

(c') 2-(4-Amino-2-methylphenyl)-1,3-propanediol (100 mg; 0.55 mmol) and cyclohexanone (150 mg) were taken up in toluene (5 ml), and a catalytic amount of p-toluenesulphonic acid was added. The solution was heated under reflux with stirring. When the condensation of water to the wall of the cooler ceased (after about 1.5 hours), the solvent was evaporated. The remaining oil (0.21 g) consisted of the imine derived from cyclohexanone and 4-(1,5-dioxaspiro[5.5]undec-3-yl)-3-methylaniline.

The imine was taken up in diethyl ether and the organic solution was washed one with 5 ml 5% aq. NaHCO$_3$. The organic layer was dried over MgSO$_4$ and evaporated at reduced pressure. The remaining oil '70 mg) consisted of 4-(1,5-dioxaspiro[5.5]undec-3-yl)-3-methylaniline, which was converted into the urea as described in Example 1(d).

EXAMPLE 3

2-(4-(3,3-dimethylureido)-2-methylphenyl)-1,3-propanediol sulphite (formula 1A, wherein R=R$^3$=CH$_3$, R$^1$+R$^2$=SO)

(a), (b') 2-(2-Methyl-4-nitrophenyl)-1,3-propanediol was prepared as described in Example 1 (a), and hydrogenated to the corresponding amino compound as described in Example 2 (b').

(c') 2-(4-Amino-2-methylphenyl)-1,3-propanediol (0.8 g; 4.4 mmol) was taken up in dichloromethane/dioxane (1/1; 20 ml), and thionylchloride (1.6 g; 13.2 mmol) was added over 30 minutes, at room temperature. The solution was heated under reflux with stirring for an additional hour. The solvent was evaporated, the residue was neutralized with a NaHCO$_3$ solution in water and the aqueous solution was thoroughly extracted with dichloromethane. The organic layers were dried over MgSO$_4$ and evaporated to dryness. The remaining oil (0.9 g) consisted of 2-(4-amino-2-methylphenyl)-1,3-propanediol sulphite (yield 90%, purity >90%).

(d) The amino compound prepared in (c') (0.9 g) was converted into its urea derivative as described in Example 1 (d). The final product consisted of 0.65 g of the title compound (purity >90%, yield 61% molar). The NMR spectrum is as follows: δ2.35 (3H,s), 3.0 (6H,s), 3.8 (2H,m), 4.15 (1H,m), 4.9 (2H,m), 6.4 (1H,s), 7.0–7.35 (3H,complex).

In an *alternative preparation*, the order of the hydrogenation and the introduction of the sulphinyl group were reversed:

(a) The 2-(2-methyl-4-nitrophenyl)-1,3-propanediol was prepared as in Example 1(a).

(b) SOCl$_2$ (1.5 ml, 0.021 mol) was added dropwise to a suspension of 1.5 g (0.0071 mol) 2-(2-methyl-4-nitrophenyl)-1,3-propanediol in 10 ml toluene and 1.5 ml diethylether, which was kept at room temperature by means of a water bath. After stirring for 1.5 hours water was carefully added. Addition of fresh water to the separated organic layer induced the formation of crystalline material. The crystals were collected by filtration and dried in vacuo. This yielded a nearly colourless material (0.7 g, 95% pure sulphite, 40% yield). The organic layer of the combined filtrates was washed with water, dried over MgSO$_4$ and evaporated at reduced pressure. The residue (0.7 g) contained 63% (GLC area %) of 2-(2-methyl-4-nitrophenyl)-1,3-propanediol sulphite.

(c) The compound prepared in step (b) (0.45 g; 1.75 mmol) was dissolved in methanol (50 ml) and a catalytic amount of 10% Pt/C was added. The reduction was carried out at room temperature, in a hydrogenation apparatus operating at atmospheric pressure. ~150 ml H$_2$ (~6 mmol) was taken up. Upon opening of the reaction vessel a mercaptan-like stench was noted. After removal of the catalyst by filtration, the reaction mixture was evaporated to dryness.

2-(4-Amino-2-methylphenyl)-1,3-propanediol sulphite constituted 90% of the product (GLC area %). This was converted into the urea derivative as described in (d) of this Example.

EXAMPLE 4

3-(3-chloro-4-(1,5-dioxaspiro[5.5]undec-3-yl)phenyl-1,1-dimethylurea (formula Ia, wherein R=Cl, R$^1$+R$^2$=cyclohexylidene, R$^3$=CH$_3$)

This compound is prepared completely analogous to the compound of example 2, i.e. the compound wherein R=CH$^3$ instead of Cl. The NMR spectrum is as follows: 1.2–2.1 (10H,complex), 3.0 (6H,s), 3.35 (1H,m), 4.0 (4H,d), 6.35 (1H,s), 7.1–7.5 (3H,complex).

EXAMPLE 5

3-(4-(1-Methoxy-2-propyl)-3-methylphenyl)-1,1-dimethylurea (formula I, wherein R=R$^1$=R$^3$=CH$_3$, R$^2$=H, n=0)

(a) 2-(2-methyl-4-nitrophenyl)-1,3-propanediol was prepared as described in Example 1(a).

(b) A slurry of 13.5 g (0.064 mol) of the compound prepared in (a) in 3.6 ml (0.046 mol) pyridine and 90 ml toluene was stirred at 70°–80° C. in an oil bath. SOCl$_2$ (14 ml, 0.20 mol) was added over a period of 10 minutes. One hour after the addition the mixture was cooled to room temperature and 50 ml water was slowly added. The toluene layer was washed with water, dried over MgSO$_4$ and evaporated at reduced pressure. The residue (15.8 g) contained 91% pure 1,3-dichloro-2-(2-methyl-4-nitrophenyl)propane; yield: nearly quantitative. The product crystallised on standing.

(c) 0.6 g Potassium-t-butoxide was added to a suspension of 1.2 g (5 mmol) of the compound prepared in (b) in 10 ml t-butanol at room temperature. A white solid (KCl) precipitated. The reaction was complete in 1 hour; 3-chloro-2-(2-methyl-4-nitrophenyl)propene was formed quantitatively.

To this mixture 2.5 ml 30% CH$_3$ONa in CH$_3$OH (14 mmol) was added at room temperature with stirring. The reaction was complete in 4 hours. After removal of the solid filtration, the solvent was flashed off. The product was taken up in chloroform and washed with water, dried over MgSO$_4$ and the chloroform was evaporated. 0.95 g of 3-methoxy-2-(2-methyl-4-nitrophenyl)-propene was isolated (92% yield; 85% purity).

(d) The compound prepared in (c) was dissolved in 30 ml CH$_3$OH and a catalytic amount of 10% Pt/C was added. The hydrogenation was carried out at room temperature in a hydrogenation apparatus at atmospheric pressure. 435 ml H$_2$ (17.4 mmol) was taken up. After removal of the catalyst by filtration, the reaction mixture was evaporated to dryness. 0.8 g of 1-methoxy-2-(4-amino-2-methylphenyl)propane was isolated (97% yield, 75% purity).

(e) The compound prepared in (d) (1.0 g; 5.6 mmol) was taken up in ethyl acetate (10 ml) and added to a saturated solution of phosgene in toluene (35 ml), with stirring at room temperature. The reaction was slowly heated to reflux and a rigorous stream of dry nitrogen was passed through the solution, in order to remove the HCl formed, and the excess $COCl_2$. After about 1 hour the reaction mixture was allowed to cool to room temperature and a saturated solution of dimethylamine in toluene (15 ml) was added. After stirring for 30 min., the solvent was flashed off.

0.4 g 3-(4-methoxypropylene-3-methylphenyl)-1,1-dimethylurea was isolated (30% yield; >90% purity).

The NMR spectrum is as follows: 1.2 (3H, 2 doublets), 2.25 (3H,s), 3.0 (6H, s), 3.0–3.5 (3H, complex), 3.35 (3H,s), 6.35 (1H,s), 6.95–7.35 (3H, complex).

EXAMPLES 6–16

By methods analogous to those of the preceding Examples, a further number of compounds were prepared, of which the details are summarised in table I. All compounds are according to Formula Ia, wherein $R^3=CH_3$ and $R=CH_3$ meta to the ureido group.

TABLE I

| Example | ($R^1 + R^2$) | melting point (°C.) |
|---|---|---|
| 6 | 3-pentylidene | 132–133 |
| 7 | cyclopentylidene | 149–151 |
| 8 | 2-butylidene (A*) | 126–128 |
| 9 | 2-butylidene (B*) | 128–130 |
| 10 | 2-butylidene (mix of 8 and 9) | — |
| 11 | 3-methyl-2-butylidene (A*) | 129–130 |
| 12 | 3-methyl-2-butylidene (B*) | — |
| 13 | 2-pentylidene | 101–103 |
| 14 | 4-heptylidene | 131–133 |
| 15 | 1-phenylethylidene | 116–118 |
| 16 | isopropylidene | 164–166 |

*Isomer separated by column chromatography of the corresponding nitro compound mixture according to formula V. The isomers marked A are faster running than those marked B.

EXAMPLE 17

Herbicidal Activity

To evaluate their herbicidal activity, compounds according to the invention were tested using as a representative range of plants: maize, Zea mays (Mz); rice, Oryza sativa (R); barnyard grass, Echinochloa crusgalli (BG); oat, Avena sativa (O); linseed, Linum usitatissiusum (L); mustard, Sinapsis alba (M); sugar beet, Beta vulgaris (SB) and soya bean, Glycine max (S).

The tests fall into two categories, pre-emergence and post-emergence. The pre-emergence tests involved spraying a liquid formulation of the compound onto the soil in which the seeds of the plant species mentioned above had recently been sown. The post-emergence tests involved two types of test, viz., soil drench and foliar spray tests. In the soil drench tests the soil in which the seedling plants of the above species were growing, was drenched with a liquid formulation containing a compound of the invention, and in the foliar spray tests the seedling plants were sprayed with such a formulation.

The soil used in the tests was a prepared horticultural loam.

The formulations used in the tests were prepared by diluting with water, solutions of the test compounds in acetone containing 0.4% by weight of an alkylphenol-/ethylene oxide condensate available under the trade mark TRITON X-155. The acetone solutions were diluted with water and the resulting formulations applied at dosage levels corresponding to 5 kg and/or 1 kg of active material per hectare in a volume equivalent to 600 liters per hectare in the soil spray and foliar spray tests, and at a dosage level equivalent to 10 kilograms of active material per hectare in a volume equivalent to approximately 3,000 liters per hectare in the soil drench tests.

In the pre-emergence tests untreated sown soil and in the post-emergence tests untreated soil bearing seedling plants were used as controls.

The herbicidal effects of the test compounds were assessed visually twelve days after spraying the foliage and the soil and thirteen days after drenching the soil, and were recorded on a 0–9 scale. A rating 0 indicates growth as untreated control, a rating 9 indicates death. An increase of 1 unit on the linear scale approximates to a 10% increase in the level of effect. A hyphen indicates not tested, or no results for another reason.

The results of the tests are set out in Table II below.

TABLE II

| Compound of Example No. | Soil Drench 10 kg/ha | | | | | | | | Dosage kg/ha | Foliar Spray | | | | | | | | Pre-emergence | | | | | | | |
|---|---|---|---|---|---|---|---|---|---|---|---|---|---|---|---|---|---|---|---|---|---|---|---|---|---|
| | Mz | R | BG | O | L | M | SB | S | | Mz | R | BG | O | L | M | SB | S | Mz | R | BG | O | L | M | SB | S |
| 1 | 7 | 9 | 8 | 9 | 9 | 9 | 9 | 9 | 5 | 6 | 6 | 7 | 7 | 8 | 9 | 9 | 9 | 4 | 0 | 9 | 6 | 6 | 8 | 9 | 4 |
| | | | | | | | | | 1 | 0 | 3 | 6 | 5 | 6 | 9 | 8 | 7 | 0 | 0 | 7 | 5 | 2 | 7 | 8 | 0 |
| 2 | 6 | 8 | 9 | 1 | 9 | 9 | 9 | 9 | 5 | 0 | 2 | 9 | 2 | 9 | 9 | 9 | 8 | 2 | 2 | 9 | 0 | 5 | 9 | 9 | 0 |
| | | | | | | | | | 1 | 0 | 2 | 7 | 0 | 9 | 9 | 9 | 8 | 0 | 0 | 7 | 0 | 3 | 8 | 9 | 0 |
| 3 | 7 | 9 | 9 | 9 | 9 | 9 | 9 | 9 | 5 | 1 | 5 | 9 | 8 | 9 | 9 | 9 | 9 | 2 | 2 | 8 | 7 | 6 | 9 | 9 | 4 |
| | | | | | | | | | 1 | 0 | 2 | 7 | 3 | 8 | 9 | 9 | 6 | 0 | 0 | 6 | 4 | 4 | 7 | 8 | 0 |
| 4 | 2 | 3 | 4 | 1 | 7 | 9 | 9 | 4 | 5 | — | — | — | — | — | — | — | — | — | — | — | — | — | — | — | — |
| | | | | | | | | | 1 | 2 | 3 | 5 | 2 | 9 | 9 | 9 | 5 | 0 | 0 | 4 | 0 | 3 | 4 | 9 | 3 |
| 5 | 6 | 8 | 9 | 9 | 9 | 9 | 9 | 9 | 5 | — | — | — | — | — | — | — | — | — | — | — | — | — | — | — | — |
| | | | | | | | | | 1 | 3 | 6 | 8 | 7 | 7 | 9 | 9 | 9 | 0 | 3 | 5 | 5 | 4 | 5 | 6 | 4 |
| 6 | 4 | 6 | 8 | 7 | 8 | 9 | 9 | 8 | 5 | 4 | 4 | 9 | 6 | 8 | 9 | 9 | 8 | 0 | 0 | 0 | 0 | 4 | 7 | 7 | 0 |
| | | | | | | | | | 1 | 2 | 2 | 9 | 6 | 8 | 9 | 9 | 8 | 0 | 0 | 0 | 0 | 1 | 6 | 6 | 0 |
| 7 | 3 | 7 | 8 | 7 | 9 | 9 | 9 | 8 | 5 | 3 | 5 | 9 | 6 | 9 | 9 | 9 | 7 | 0 | 0 | 3 | 4 | 2 | 8 | 8 | 4 |
| | | | | | | | | | 1 | 0 | 0 | 8 | 5 | 6 | 9 | 9 | 6 | 0 | 0 | 2 | 0 | 0 | 7 | 8 | 0 |
| 8 | 3 | 6 | 9 | 6 | 8 | 9 | 9 | 8 | 5 | 4 | 3 | 8 | 6 | 8 | 9 | 9 | 8 | 0 | 0 | 4 | 0 | 5 | 7 | 8 | 0 |
| | | | | | | | | | 1 | 3 | 0 | 8 | 5 | 8 | 9 | 9 | 8 | 0 | 0 | 0 | 0 | 3 | 5 | 6 | 0 |
| 9 | 2 | 7 | 8 | 7 | 9 | 9 | 9 | 6 | 5 | 6 | 5 | 9 | 7 | 9 | 9 | 9 | 7 | 0 | 0 | 5 | 2 | 2 | 7 | 7 | 0 |
| | | | | | | | | | 1 | 2 | 2 | 8 | 6 | 8 | 9 | 9 | 5 | 0 | 0 | 0 | 0 | 0 | 5 | 7 | 0 |
| 11 | 4 | 6 | 8 | 6 | 8 | 9 | 9 | 8 | 5 | 4 | 5 | 9 | 6 | 8 | 9 | 9 | 8 | 0 | 0 | 0 | 0 | 2 | 6 | 7 | 0 |
| | | | | | | | | | 1 | 2 | 2 | 9 | 6 | 8 | 9 | 9 | 8 | 0 | 0 | 0 | 0 | 0 | 0 | 5 | 0 |
| 12 | 3 | 6 | 8 | 6 | 8 | 9 | 9 | 8 | 5 | — | — | — | — | — | — | — | — | — | — | — | — | — | — | — | — |
| | | | | | | | | | 1 | 2 | 2 | 8 | 5 | 8 | 9 | 9 | 8 | 0 | 0 | 0 | 0 | 0 | 5 | 7 | 0 |

TABLE II-continued

| Compound of Example No. | Soil Drench 10 kg/ha | | | | | | | | Dosage kg/ha | Foliar Spray | | | | | | | | Pre-emergence | | | | | | | |
|---|---|---|---|---|---|---|---|---|---|---|---|---|---|---|---|---|---|---|---|---|---|---|---|---|---|
| | Mz | R | BG | O | L | M | SB | S | ha | Mz | R | BG | O | L | M | SB | S | Mz | R | BG | O | L | M | SB | S |
| 13 | — | — | — | — | — | — | — | — | 5 | — | — | — | — | — | — | — | — | | | | | | | | |
| | | | | | | | | | 1 | | | | | | | | | | | | | | | | |
| 14 | 2 | 3 | 7 | 8 | 9 | 8 | 9 | 4 | 5 | 3 | 2 | 8 | 6 | 8 | 9 | 9 | 6 | 4 | 0 | 4 | 2 | 0 | 6 | 6 | 0 |
| | | | | | | | | | 1 | 3 | 5 | 9 | 7 | 9 | 9 | 9 | 8 | 0 | 3 | 4 | 0 | 0 | 7 | 9 | 0 |
| 15 | 1 | 2 | 2 | 4 | 8 | 9 | 9 | 6 | 5 | 2 | 2 | 8 | 4 | 8 | 9 | 9 | 6 | 0 | 0 | 2 | 0 | 0 | 3 | 5 | 0 |
| | | | | | | | | | 1 | 4 | 3 | 9 | 4 | 8 | 9 | 9 | 6 | 0 | 0 | 0 | 0 | 0 | 8 | 9 | 0 |
| 16 | 6 | 9 | 9 | 8 | 9 | 9 | 9 | 9 | 5 | 0 | 0 | 7 | 2 | 8 | 9 | 9 | 2 | 0 | 0 | 0 | 0 | 0 | 6 | 9 | 0 |
| | | | | | | | | | 1 | 7 | 9 | 9 | 7 | 9 | 9 | 9 | 9 | 5 | 3 | 9 | 7 | 9 | 9 | 9 | 6 |
| | | | | | | | | | | 2 | 7 | 7 | 5 | 9 | 9 | 9 | 9 | 0 | 0 | 7 | 2 | 4 | 9 | 9 | 3 |

What is claimed is:

1. A compound of general formula Ia:

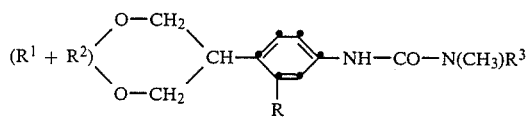

(Ia)

wherein R represents a chlorine atom or a methyl group; $R^3$ represents $CH_3$ and $R^1$ and $R^2$ together represent a cyclohexylidene group.

2. A compound according to claim 1 wherein R represents a chlorine atom.

3. A compound according to claim 1 wherein R represents a methyl group.

4. A compound of the formula

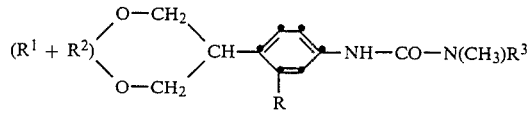

wherein R represents a halogen atom or a methyl group; $R^3$ represents H, $CH_3$ or $OCH_3$ and $R^1$ and $R^2$ together represent a cyclopentylidene group.

5. A compound according to claim 4 characterized in that $R^3$ represents a methyl group.

6. A herbicidal composition, which comprises a herbicidally effective amount of a compound according to claim 1 together with at least one carrier.

7. A composition according to claim 6, which comprises at least two carriers, at least one of which is a surface-active agent.

8. A method of combating undesired plant growth at a locus, which comprises treating the locus with a herbicidally effective amount of a compound according to claim 1.

9. A method of combating undesirable plant growth at a locus, which comprises treating the locus with a herbicidally effective amount of a compound according to claim 4.

* * * * *